(12) United States Patent
Glennon et al.

(10) Patent No.: US 6,518,297 B2
(45) Date of Patent: Feb. 11, 2003

(54) SELECTIVE 5-$HT_6$ RECEPTOR LIGANDS

(75) Inventors: Richard A. Glennon, Midlothian, VA (US); Bryan Roth, Moreland Hills, OH (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 10/042,265

(22) Filed: Jan. 11, 2002

(65) Prior Publication Data

US 2002/0103383 A1 Aug. 1, 2002

Related U.S. Application Data

(62) Division of application No. 09/857,777, filed as application No. PCT/US99/29219 on Dec. 10, 1999, now Pat. No. 6,403,808.
(60) Provisional application No. 60/111,787, filed on Dec. 11, 1998.

(51) Int. Cl.[7] ..................... C07D 209/04; A61K 31/404
(52) U.S. Cl. ....................................... 514/415; 548/491
(58) Field of Search ........................... 548/491; 514/415

(56) References Cited

U.S. PATENT DOCUMENTS 5,496,957 A * 3/1996 Glennon ..................... 548/491

FOREIGN PATENT DOCUMENTS

WO      WO 95/30655    * 11/1995

OTHER PUBLICATIONS

Glennon, J. Med. Chem. 37:1929–1935 (1994).
Roth, J. Pharmacol. Exp. Ther. 268:1403–1410 (1994).
Glennon, J. Med. Chem., 32:1921–1926 (1989).

* cited by examiner

*Primary Examiner*—Deborah C. Lambkin
*Assistant Examiner*—Golam M. M. Shameem
(74) *Attorney, Agent, or Firm*—Whitham, Curtis & Christofferson, P.C.

(57) ABSTRACT

Compounds which have enhanced affinity and selectivity for 5-$HT_6$ receptors have been identified. These compounds can be used therapeutically in the treatment of mental disorders via administration in a pharmacologically acceptable delivery route to a patient in need thereof, or can be used to identify antagonists of 5-$HT_6$ receptors by well known screening methodologies which could themselves be used in the treatment of mental disorders.

2 Claims, 1 Drawing Sheet

SELECTIVE 5-HT$_6$ RECEPTOR LIGANDS

RELATED APPLICATIONS

This is a divisional application of application U.S. Ser. No. 09/857,777 filed Aug. 20, 2001, now U.S. Pat. No. 6,403,808 is a 371 of and International Application No. PCT/US99/29219 filed Dec. 10, 1999 that designated the U.S. and claims the benefit of provisional application No. 60/111,787 filed Dec. 11, 1998 and are hereby incorporated therein by reference.

This invention was discovered in the performance of U.S. government supported research under grants NIMH KO2MH01366 and NCEMS GM52213, and the U.S. government may have certain rights in the invention.

DESCRIPTION

BACKGROUND OF THE INVENTION

1. Field of the Invention

The present invention relates to the synthesis of novel ligands selective for a subgroup of receptors for serotonin (5-HT). While there are seven subgroups of 5-HT receptors, this invention is selective for the 5-HT$_6$ subgroup. This invention also relates to the synthesis of novel ligands selective for the 5-HT$_6$ subgroup receptor that act as agonists to the natural ligands for this receptor. The invention also relates to the creation of novel ligands that act as antagonists to the 5-HT$_6$ receptor. The invention further relates to use of said compounds to treat mammals adversely affected by conditions mediated by the 5-HT$_6$ receptor.

2. Description of the Prior Art

Serotonin receptors have been divided into a number of families and subfamilies (5-HT$_1$–5-HT$_7$) and approximately 14 populations have been cloned. One of the newest populations identified is the 5-HT$_6$ subgroup. It has been observed that various tricyclic psychotropic agents (neuroleptics, antidepressants, and atypical neuroleptics agents) bind the 5-HT$_6$ receptor with nanomolar affinities (Roth et al. J. Pharmacol. Exp. Ther. 1994, 268, 1403–1410). A rat 5-HT$_6$ receptor was first cloned in 1993 and, more recently, the same group described the cloning of a human 5-HT$_6$ receptor. The 5-HT$_6$ serotonin receptors are members of the G-protein superfamily, are positively coupled to an adenylate cyclase second messenger system and are found primarily in the central nervous system. Serotonin bound to the 5-HT$_6$ receptor subgroup causes an activation of the adenylate cyclase enzyme, with concomitant increased levels of intracellular cAMP. Although the exact physiological function and clinical significance of the 5-HT$_6$ receptor subgroup is not known, as noted above, many anti-psychotic agents bind these receptors with high affinity. Also, in rats that do not express 5-HT$_6$ receptors, the animals behave in a manner that seems to involve an increase in cholinergic function, suggesting that 5-HT$_6$ specific ligands might be of value in the treatment of anxiety-related disorders and memory deficits.

Upon binding to cellular receptors, ligands may act as agonists or antagonists to endogenous receptor-ligand function. In the case of the 5-HT$_6$ receptor, several specific ligands have been discovered which act as 5-HT$_6$ specific antagonists, but prior to the present invention, selective ligands which act as agonists to the 5-HT$_6$ receptor were unknown.

SUMMARY OF THE INVENTION

It is an object of the invention to create derivatives of serotonin (5-HT) that specifically bind the 5-HT$_6$ receptor subgroup of the serotonin receptor family. It is another object of this invention to create 5-HT$_6$-selective ligands that act as agonists when bound to the 5-HT$_6$ receptor. It is further an object of this invention to create 5-HT$_6$-selective ligands that act as antagonists when bound to the 5-HT$_6$ receptor. Furthermore, the compounds of the present invention that possess antagonist activity are tryptamine derivatives and are structurally unrelated to previously described 5-HT$_6$ antagonists. It is further an object of this invention to administer 5-HT$_6$ selective ligands to animals to determine the physiological and biochemical effects of specific activation and inhibition of 5-HT$_6$ receptor function. Finally, it is an object of this invention to treat mental disorders mediated by 5-HT$_6$ function by administering to treatment subjects the 5-HT$_6$-selective agonists and antagonist compounds described herein.

Various indolealkylamines, including serotonin(5-HT) and 5-methoxytryptamine, have been observed to bind the 5-HT$_6$ receptor with high affinity and produce a potent dose-dependent increase in cAMP levels. These tryptamines, however, are non-selective and bind at multiple families of 5-HT receptors. According to the invention, various modifications of 5-HT have been made to generate ligands with selectivity for the 5-HT$_6$ receptor. An analog of 5-HT with a 2-methyl substituent introduced (2-methyly-5-HT) binds the 5-HT$_6$ receptor with an affinity equivalent to that of the parent compound. The above analog is selective for the 5-HT$_6$ and 5-HT$_3$ receptors and binds at the 5-HT$_6$ subgroup with a 20 fold greater affinity than at 5-HT$_3$ receptors.

A 2-methyl analog of 5-methoxytryptamine, 5-methoxy-2-methyltryptamine, binds to the 5-HT$_6$ receptor with an affinity comparable to 2-methyl-5-HT. However, 5-methoxy-2-methyltryptamine lacks affinity for 5-HT$_3$ receptors. Thus, 5-methoxy -2-methyltryptamine presents a ligand with specificity for the 5-HT$_6$ receptor subgroup. In the present invention, the 5-methoxy-2-methyltryptamine compound has been modified and several of its alkyl derivatives bind with comparable affinity and activate adenylate cyclase activity at levels comparable to serotonin. Furthermore, one derivative, 5-methoxy-2-phenylotryptamine, binds to the 5-HT$_6$ receptor with a high affinity but the phenyl addition renders the compound an antagonist to 5-HT stimulated adenylate cyclase activity.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
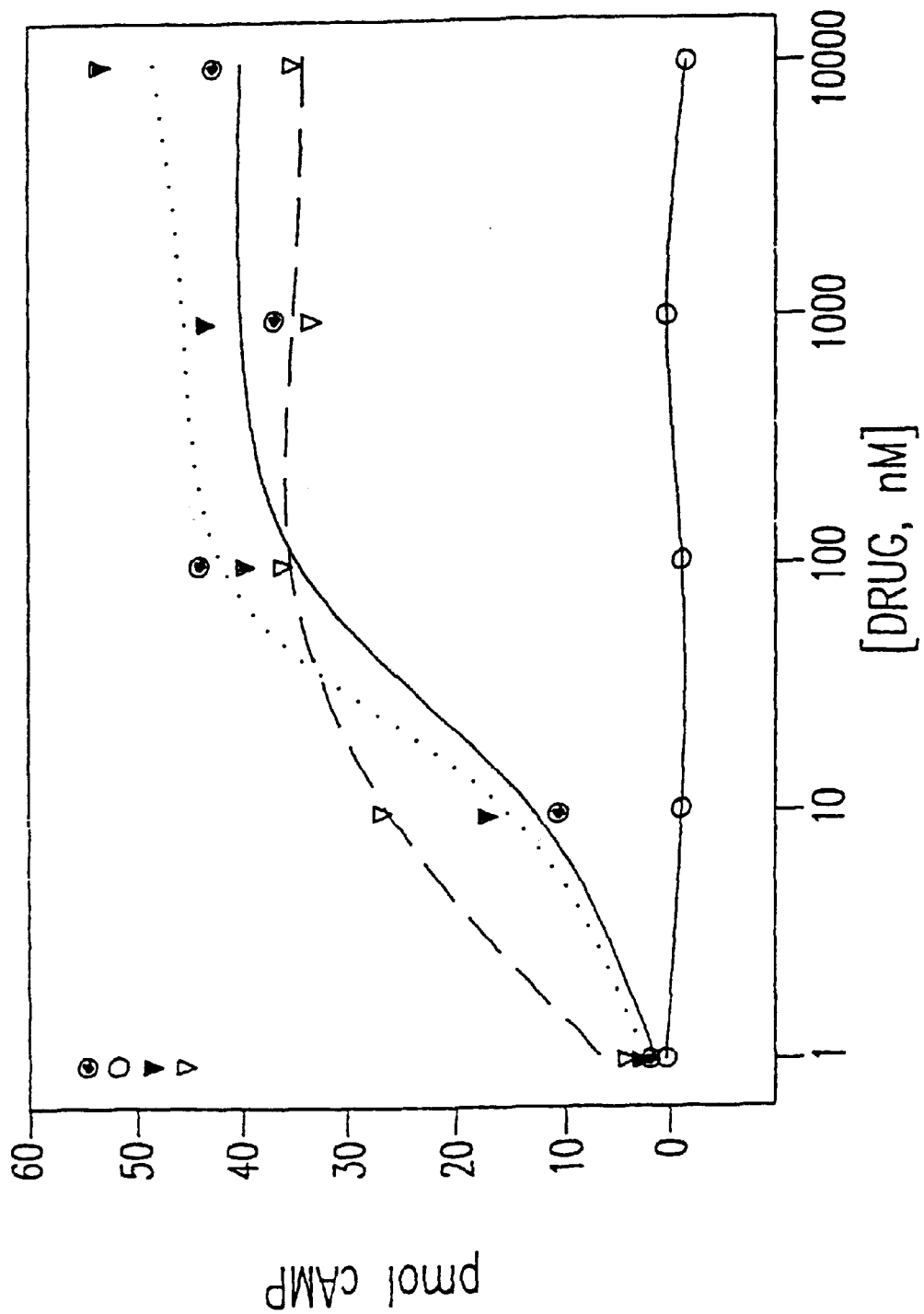
FIG. 1 is a graph showing the adenylate cyclase activity observed with several compounds of the invention.

The invention provides novel tryptamine derivative compounds with selectivity for the 5-HT$_6$ receptor subgroup. For the present purpose, an agent is termed selective when it displays an affinity for 5-HT$_6$ receptors that is tenfold higher than affinities it displays for other related receptor populations. The invention further provides a method using said compounds to receptor subtype 5-HT$_6$ as agonists, or as antagonists to serotonin. The compounds of the invention can be used either as the free base or as the pharmaceutically acceptable acid-addition salt form, for example, hydrochloride, hydrobromide, tartrate, and maleate. They may be used in oral or injectable pharmaceutical preparations as prophylactic and acute-phase remedies for the relief and reversal of serotonin-regulated symptoms. They may be used alone or in combination with each other or other known medications. Finally, said compounds may be used as above for determining 5-HT$_6$ receptor function.

Serotonin (5-hydroxy tryptamine, or 5-HT) is a product of tryptophan metabolism and is a tryptamine derivative that is a potent neurotransmitter. Serotonin is a well-characterized tryptamine derivative which regulates calcium ion channels on the surface of nerve and muscle cells. Many mental disorders in humans are associated with fluctuations in serotonin levels and are effectively treated with drugs which specifically interact with serotonin receptors or that block the reuptake of serotonin into the presynaptic axon terminals, suggesting that serotonin dysregulation may be involved in various mental disorders. Some serotonin receptor ligands and are clinically approved as drugs for the treatment of migraine headaches, depression, high blood pressure, and psychosis.

Generally, tryptamine derivatives are non-selective and bind at multiple 5-HT receptor subgroups. Serotonin is no exception and binds at the various subfamilies of the 5-HT receptor, including the 5-HT$_6$ subgroup where it is a potent activator of adenylate cyclase enzyme activity. Serotonin has the chemical formula:

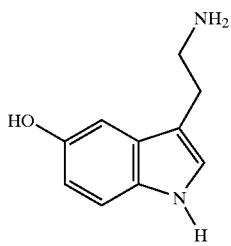

Some modifications of serotonin result in loss of affinity for various 5-HT receptor subgroups. It had previously been thought that introduction of a 2-methyl substituent to 5-HT was not tolerated by any 5-HT receptors but the 5-HT$_3$ subgroup. Thus, prior to identification of the 5-HT$_6$ receptor, 2-°methylation of 5-HT was thought to render the product selective for the 5-HT$_3$ subgroup. We have found that the two methyl derivative of 5-HT, 2-methyl-5-HT has a high affinity for the 5-HT$_6$-receptor. In fact, 2-methyl-5-HT binds the 5-HT$_6$ receptor with a 20 fold greater affinity over 5-HT$_3$ receptors. The 5-HT$_6$-selective ligand 2-methyl-5-methoxytryptamine contains a primary amine, presenting an obstacle to the compound crossing the blood brain barrier and also rendering the compound vulnerable to rapid metabolism due to oxidative deamination. Our discovery that a methyl substituent at the 2 position was tolerated by the 5-HT$_6$ receptor, together with the previous observation that O-°methylation of 5-HT abolishes affinity for 5-HT$_3$ receptor, led to the present invention.

To address the above limitations of 2-methyl-5-methoxytryptamine, several derivative compounds were synthesized that were lipophilic and also might be less prone to rapid metabolism. N,N-dimethyl substituents were added to 2-methyltryptamine to create 2-methyl-N,N-dimethyltryptamine (Ki=308 nM). Re-introduction of the methoxy group to this compound, to form 2-methyl-5-methoxy-N,N-dimethyltryptamine resulted in a compound (Compound A) with an affinity for the 5-HT$_6$ receptor of Ki=60 nM. Homologation of the 2-methyl substituent of the above compound to form 2-ethyl-5-methoxy-N,N-dimethyltryptamine resulted in a ligand with an increased affinity for the 5-HT$_6$ of Ki=16 nM (Compound B). To determine whether or not greater bulk additions could be added in place of a methyl or ethyl group, the 2-phenol derivative of the 2-methyl-5-methoxy-N,N-dimethyltryptamine was generated. This compound D binds the 5-HT$_6$ receptor with a Ki=20 nM. These derivatives were of the general formula 1

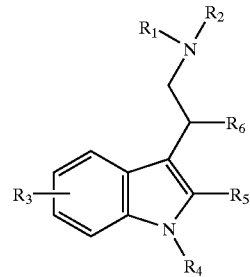

where $R_1$ and $R_2$=H or $CH_3$, $R_3$=H, OH, $OCH_3$, or a substituted or unsubstituted alkyl, $R_4$=H, $CH_2$-phenyl, $SO_2$-phenyl, or $CH_2$ as part of a substituted or unsubstituted alkyl ring connecting $R_4$ and $R_5$, $R_5$=H, $CH_3$, or $CH_2$ as part of a substituted or unsubstituted alkyl ring connecting $R_5$ with either $R_4$ or $R_6$, $R_6$=H, $CH_3$, or $CH_2$ as part of a substituted or unsubstituted alkyl ring connecting $R_6$ and $R_5$.

The compounds of the invention and the pharmaceutically acceptable salts of the compounds of the invention can be used in the form of pharmaceutical preparations. The preparations can be administered orally, for example in the form of tablets, coated tablets, dragees, hard and soft gelatin capsules, solutions, emulsions or suspensions. The administration can be effected rectally, for example in the form of suppositories, or parenterally, for example in the form of injection solutions.

The compounds of the invention can be processed with pharmaceutically inert, inorganic or organic carriers for the production of pharmaceutical and research preparations. The preparations can contain preservatives, solubilizers, wetting agents, emulsifiers, sweeteners, colorants, flavorants, salts for varying the osmotic pressure, buffers, masking agents or antioxidants. They can also contain still other therapeutically valuable substances.

The compounds of the present invention can also be radiolabelled and used to identify other 5-HT$_6$, ligands using techniques common in the art. This can be achieved by incubating the receptor in the presence of a ligand candidate plus an equimolar amount of radiolabelled compound of the invention. Ligands selective for 5-HT$_6$ are then revealed as those that are not significantly displaced by the compounds of the present invention.

Another embodiment of the invention can be the administration of the compounds of the invention to animals in drug discrimination assays. In a drug discrimination paradigm, animals (usually rats) can be trained to recognize the effects of a given agent. Once trained, these animals can be used in tests of stimulus generalization to identify other agents that produce similar effects (i.e., agonists), or the animals can be used in tests of stimulus antagonism to identify agents that block or antagonize (i.e., antagonists) the effects of the training drug. Hence, the procedure can be used to identify agonists that produce an effect common to the training drug, more antagonists that can block the effects of the training drug. Specifically, with a 5-HT$_6$-selective agonist as training drug, the animals can be used to identify other 5-HT$_6$ agonists and to identify 5-HT$_6$-antagonists.

One family of compounds contemplated for use in this invention is represented by the formula 2

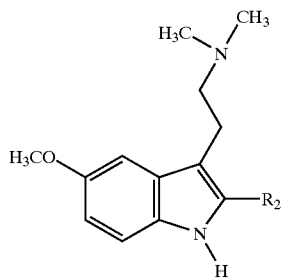

wherein R₂ is selected from the group consisting of small alkyls (e.g., methyl, ethyl, n-propryl) aryl (e.g. phenyl) and arylalkyls.

Another family of compounds for use in this invention is represented by formula 3

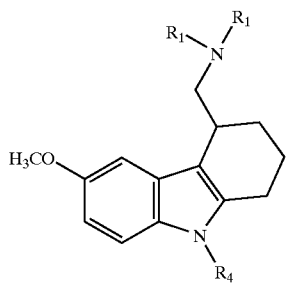

wherein R₁ is selected from the group consisting of lower alkyls such as ethyl and propyl, methyl and hydrogen, and can be the same or different at each location, and R₄ is from the group comprising H, CH₂-phenyl, or SO₂-phenyl.

Another family of compounds for use in this invention is represented by formula 4

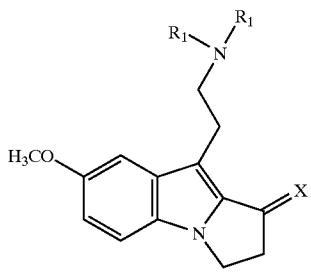

wherein X is selected from the group consisting of oxygen or 2H and R₁ is H or lower alkyls such as methyl, ethyl, or propyl.

The following examples illustrate the present invention in more detail. However, they are not intended to limit its scope in any manner.

EXAMPLE 1

Synthesis of 2ethyl-5-methoxy-N,N-dimethyltryptamine maleate (Compound B). A 2.5M solution of nBuLi (1.75 ml. 4.38 mmol) was added in a drop wise manner to a stirred solution of 2-methyl-5-methoxy-N,N-dimethyltryptamine (compound A in the examples below) free base (1.00 g, 4.33 mmol) in dry THF (7 mL) at −78° C. under N₂.

After stirring the reaction mixture for five minutes, the cooling bath was removed and CO₂ gas was passed into the solution for 10 minutes. The solvent was removed at 0° C. under reduced pressure to give a transparent solid. The flask was flushed with N₂ and dry THF (7 mL) was added. The reaction mixture was degassed at −150° C. under reduced pressure of 1 mMHg, then allowed to warm to −78° C.; 1.7M tNuLi (2.8 mL, 4.8 mmol) was added in a drop wise manner. The solution was kept at −78° C. for three hours. The reaction make sure was acidified with a saturated ethereal solution of HCl. Anhydrous Et₂O was added to the resulting suspension and the supernatant was decanted. The residue was heated at 100° C. under reduced pressure for 20 minutes. The resulting residue was purified by flash chromatography on silica gel (CH₂Cl₂/MeOH; 12:1) to give 0.17 g of a bright yellow oil (16%). ¹H-NMR(CDCl₃) d 8.06 (s, 1H, J=8.67 HZ), 6.98 (s, 1H), 6.76 (dd, 1H, J=2.34, 8.73 HZ), 3.84 (s, 3H) 2.91–2.87 (m, 2H), 2.71 (q, 2H, J=7.38 HZ), 2.57–2.52 (m, 2H) 2.38 (s, 6HJ)1.25 (t, 3H, J=7.38 HZ).The maleate salt was prepared and recrystallized from an EtOAc/Et₂O mixture; mp 123° C.

EXAMPLE 2

Magnesium turnings and NH₄Cl were added to a solution of Example 11 infra (1-Benzenesulfonyl-5-methoxy-2-n-propyl-N,N-dimethyl tryptamine, free base; 259 mg, 0.65 mmol) in MeOH (17 mL) and the mixture was allowed to stir at room temperature for one-hour. Saturated NH₄Cl solution was added and the reaction mixture was extracted with CH₂Cl₂. The organic portion was dried (MgSO₄) and the solvents was removed under reduced pressure. The residue was purified by flash chromatography on silica gel (CH₂Cl₂/MeOH; 9:1) to give 75 mg of a bright yellow oil. ¹H-NMR (CDCl₃) 7.71 (brs, 1H), 2.89–2.83 (m, 2H), 2.69 (t, 2H, J=7.56 Hz), 2.53–2.47 (m, 2H), 2.36 (s, 6H), 1.68 (tq, 2H, J=7.28, 7.56 HZ), 0.98 (t, 3H,J=7.28 HZ). The salt was prepared and recrystallized from acetone; mp 146–147° C.

EXAMPLE 3

5-methoxy-2-phenyl-N,N-dimethyltryptamine oxalate (Compound D). 5-methoxy-2-phenylindole (3 g, 13.44 mmol) was added to a stirred ice-cooled solution of 1-dimethylamino-2-nitroethylene (1.56 g, 13.44 mmol) in trifluoracetic acid (8 ml). The resulting mixture was allowed to stir under N₂ at room temperature for 30 minutes and was then poured into ice/water. The solution was extracted with EtOAc and the organic portion was washed consecutively with saturated NaHCO₃ solution, H₂O, and then brine. The organic portion was dried (MgSO₄) and solvent was removed under reduced pressure. The residue was recrystallized from CH₂Cl₂/hexane to give 2.36 g (60%) of a red powder. ¹H-NMR (acetone-d6) d 8.82 (brs, 1H), 3.92 (s, 3H), IR (Kbr)1601, 1475, 1251 cm⁻¹. A solution of this material (2 g, 6.75 mmol) in dry THF was added in a drop wise manner to a cooled 0° C. suspension of LiALH₄ (1.54 g, 40.5 mmol)in dry THF under N₂. The reaction mixture was heated at reflux for one-hour and then allowed to stand at room temperature overnight. The resulting mixture was quenched with H₂O then 15% NaOH solution. Celite was added and the solution was filtered. The solvent was removed under reduced pressure. The residue was purified by flash chromatography on silica gel (CH₂Cl₂/MeOH; 9:1) to give 1 g (55%) of the primary amine as an oil. ¹H-NMR (CDCl₃) d 8.19 (brs, 1H, J=2.37 HZ), 6.88 (dd, 1H, J=2.24, 8.75 HZ), 3.89 (s, 3H), 3.04 (brs, 4H). IR(KBr) 3397, 3347 cm⁻¹. Sodium cyanoborohydride (510 mg, 8.12 mmol) was added to a solution of the primary amine (700 mg, 2.63 mmol) and 37% aqueous CH₂O in MeCN (10 mL) at room temperature. The resulting mixture was adjusted to pH 5 with HOAc and was allowed to stir at room temperature overnight. A 15% solution of NaOH was added to neutralize the mixture and the mixture was extracted with. CH₂Cl₂. The combined organic portion was washed with saturated NaHCO$_3$ solution and brine. The organic portion was dried (MgSO$_4$) and solvent was removed under reduced pressure. The residue was purified by flash chromatography on silica gel (CH$_2$Cl$_2$/MeOH; 9:1) to give 195 mg of 5-methoxy-2-phenyl-dimethyltryptamine free base as a white powder. $^1$HNMR (CDCl$_3$) d 8.05 (brs, 1 h), 7.56–7.53 (m, 2H), 7.49–7.44 (m, 2H), 7.39–7.34 (m, 1H), 7.29, 7.25 (m, 1H), 7.11 (d, 1H, J=2.25 HZ). 6.87 (dd, 1H, J=2.52, 8.73 HZ), 3.89 (s, 3H), 3.13–3.08 (m 2H), 2.72–2.66 (m, 2H), 2.39 (s, 6H). Although the HCl salt has previously been reported, difficulties in his purification led to isolation of the product has its salt; after recrystallization from acetone.

EXAMPLE 4

4-dimethylaminomethyl-9-benzyl-6-methoxy-1,2,3,4, tetrahydrocarbazole hydrochloride (Compound E). A mixture of 4-methoxyphenyl)benzylamine (42 g 0.2 mol) and ethyl 6-bromocyclohexanone Carboxylate (J. Org Chem 1961, 26, 22) (24.9 g, 0.1 mol) were heated at reflux in dry benzene (250 mL) for 24 hours. The reaction mixture was cooled and precipitated (4-methoxyphenyl) benzylamine hydrobromide was separated by filtration. The benzene extract was concentrated and fused zinc chloride (40 g) was added in reflux in absolute ethanol (125 mL) for six hours. The cooled mixture was slurred in H$_2$O (250 mL) and extracted with (Et$_2$O; 4×200 mL). The combined ether extracts were washed with 5% HCl (100 mL), followed by brine solution and dried with MgSO$_4$. The ether extract was evaporated under reduced pressure to give crude ethylester of title compound which was treated with a solution of KOH (50 g) in H$_2$O (150 mL) and CH$_3$OH (150 mL) at reflux temperature for three hours. The solution was evaporated to dryness under reduced pressure, the resulting residue was dissolved in H$_2$O (250 mL) and the aqueous solution was extracted with Et$_2$O and acidified with 10% HCl. The resulting solid was dried to give 22 g (33%) of title compound and was recrystallized from 1s.PrOH—H2). Mp 212–214° C. To a mixture of sodium hydride (0.96 g, 0.04 mol) in dry benzene (200 mL) was added portion wise 9-benzyl-6-methoxy-1,2,3,4-tetrahydro-4-carboxylic acid (14.00 g, 0.04 mol) and the mixture was stirred for one-hour. Thionoyl chloride (3.00 mL, 0.04 mol) was added slowly in the stirring was continued for 30 minutes. The resulting solution was poured into aqueous dimethylamine solution (40%)(36.50 mL) with ice bath cooling. The mixture was third for one-hour, washed with 100 mL H$_2$O, NaHCO$_3$ (50 mL) and saturated brine solution (50 mL), and dried with MgSO$_4$, diluted with n-pentane (200 mL) and cooled to give 4-dimethylaminocarbonyl-9-benzyl-6-methoxy-1,2,3,4-tetrahydrocarbazole (9.10 g, 60%) mp 153–155° C. To a stir it solution of LialH$_4$(4.71 g, 94.2 mmol) in dry THF was added portion wise 4-dimethylaminocarbonyl-9-benzyl-6-methoxy-1,2,3,4-tetrahydrocarbazole (9.00 g, 24.8 mmol) and the mixture was heated under reflux for five hours the reaction mixture was cooled water (5.0 mL) NaOH solution (5.0 mL) was added and filtered. The filtrate was evaporated to dryness to give 4-dimethylamino-9-benzyl6-methoxy-1, 2,3,4-tetrahydrocarbazole (8 g, 92%) . The free base was dissolved in either in converted to the salt using ethereal hydrochloride and recrystallized from a mixture of EtOH and Et$_2$O. Mp 238–240° C.

EXAMPLE 5

Compound F is known and was prepared according to the following patent procedure:4-aminomethyl-9-benzyl-1,2,3, 4-tetrahydrocarbazoles, U.S. Pat. No. 3,939,177, Feb. 17, 1976.

EXAMPLE 6

Compound G Sodium metal was added portion wise over a thirty minute period to a stirred solution of 4-(dimethylaminomethyl)-9-benzyl-6-methoxy-1,2,3,4-tetrahydrocarbazole (4 g, 0.01 mol) in liquid NH$_3$ (300 mL). NH$_4$Cl (3.0 g) was added until the blue-collar of the mixture dissipated. The NH$_3$ was evaporated, water (50 mL) was added in the mixture was extracted with CH$_2$CL$_3$. The combined organic portion was washed with water (50 mL), brine (50 mL), dried (MgSO$_4$) and evaporated to give an oil. The oil was purified by column chromatography (CHCL$_3$/ MeOH; 9:1) and converted to an oxalate salt. The salt was recrystallized from anhydrous Et$_2$O/absolute EtOH to give 1.8 g of the desired target as a white powder. $^1$H-NMR (CDCl$_3$, free base) d 8.10 (s, 1H, NH), 7.20 (t, 1H, ArH), 6.90 (d, 1H, ArH), 6,70 (dd, 1H, ArH), 3.80 (s, 3H, OCH3), 3.40 (t, 1H, CH), 3.15 (d, 1H, CH), 3.0 (t, 1H, CH)3.00 (t, 1H, Ch), 2.82 (s, 6H 2XCH3), 2.63–2.73 (m, 2H, CH2), 2.23 (m, 1H, CH) 1.8–2.0 (m, 3H, CH2-CH).

EXAMPLE 7

A mixture of Compound G as free base (0.5 g, 1.94 mmol) and sodium hydride (60%) (0.085 g, 3.54 mmol) was heated at 100° C. under nitrogen until the evolution of H$_2$ gas ceased. The resultant was dissolved in anhydrous DMF and benzenesulfonylchloride (0.30 mL, 2.35 mmol) was added drop wise at 0° C. The reaction mixture was stirred at room temperature overnight. Saturated NaHCO$_3$ solution was added and extracted with CH2Cl$_2$ (3×25 mL). The organic layer was dried over MgSO$_4$ and the solvent was removed under pressure. The residue was purified by column chromatography (CH$_2$Cl$_2$/MeOH; 9:1) as eluent to give an oil (0.60 g, 76%) and converted to hydrochloride salt. The hydrochloride salt was recrystallized from ethanol and anhydrous ether mp 259–261° C.

EXAMPLE 8

6,7,8,9-tetrahydro-2-methoxy-10-(N,N-dimethylaminoethyl)pyridol[1,2-a]indole-9-one Oxalate (I). A mixture of 5-methoxy-N,N-dimethyltryptamine (free base) (2.00 g, 9.17 mmol) and 60% NaH (0.41 g, 10.1 mmol) was heated at 100° C. under N$_2$ until evolution of gas had ceased. The resultant mass was dissolved in anhydrous DMF (25 ml) and anhydrous g-butryolactone 1.4 mL, 18.2 mmol) was added in dropwise manner at room temperature. The reaction mix was heated at reflux for 20 h, cooled to 0° C., and acidified by the addition of an ethereal solution of HCl. Additional Et$_2$O was added to the resulting suspension and the supernatant was decanted. The residue was dissolved in PPE (52.5 mL) and CHCl$_3$ (100 mL) and the reaction mixture was heated at reflux for 3 h under N$_2$. The resulting mixture was neutralized by the addition of 15% NaOH solution at ice-bath temperature, and extracted with CH$_2$Cl$_2$. The organic portion was dried (MgSO$_4$) and solvent was removed under reduced pressure. The residue was purified by flash chromatography on silica gel (CH$_2$Cl$_2$/MeOH; 20:1 ) to give 0.52 g (20%) of 6,7,8,9-tetrahydro-2-methoxy-10-(N,N-dimethylaminoethyl)pyridol[1,2-a]indole-9-One free base as a yellow oil. $^1$H-NMR (DMSO-d$_6$) ☐ 7.35 (d, 1H, J=8.79 Hz) 7.18 (s, 1H), 6.88 (d, 1H, J=8.85 Hz), 4.06 (t, 2H, J=6.60 Hz), 3.80 (s, 3H), 3.42–3.36(m, 2H), 3.17–3.12 (m, 2H), 2.85 (s, 6H), 2.66–2.62 (m, 2HO. IR (CHCl$_3$) 1648$^{cm}$ $_{-1}$. A small sample was converted to the oxalate salt; mp 191–192° C.

EXAMPLE 9

6,7,8,9-tetrahydro-2-methoxy-10-(N,N-dimethylinoethyl)pyridol[1,2-a]indole Oxalate (J). A solution of 1.0 M borane/THF (2 mL, 2 mmol) was added ion a dropwise manner to ice-bath cooled 6,7,8,9-tetrahydro-2-methoxy-10-(N,N-dimethylaminoethyl)pyridol[1,2-a] indole-9-one Oxalate (290 mg, 1.01 mmol) under N$_2$. The reaction mixture was allowed to stir at room temperature for 2 h. Acetone (3 ml) was added, and the reaction mixture was heated at reflux for 1 h to quench the unreacted borane reagent. The solvent was removed under reduced pressure. The residue was purified by flash chromatography on silica gel (hexane/EtOAc; 4:1) to give 207 mg (75%) of a light yellow oil. $^1$H-NMR (DMSO-d$_6$) ◻ 7.34 (d, 1H, J=8.85 Hz) 7.21 (s, 1H), 4.08 (t, 2H, J=6.65 Hz), 3.79 (s, 3H), 3.40–3.35 (m, 2H), 3.30–3.25 (m, 2H), 3.06–3.01 (m, 2H) 2.83 (s, 6H) 1.76–1.69 (m, 2H), 1.40–1.31 (m, 2H). A small portion was converted to its oxalate salt; mp 114–115° C.

EXAMPLE 10

1-Benzenesulfonyl-5-methoxy-N,N,-dimethyltryptamine oxalate. A mixture of 5-methoxy-N,N-dimethyltryptamine (free base) (4.35 g, 19.93 mmol) and 60% NaH (0.87 g, 21.75 mmol) was heated at 100° C. under N$_2$ until evolution of H$_2$ gas ceased. The resultant mass was dissolved in anhydrous DMF (21 ml) and benzenesulfonyl chloride (2.8 ml, 21.94 mmol) and 60% NaH (0.87 g, 21.75 mmol) was added in a dropwise manner at 0° C. The reaction mixture was allowed to stir at room temperature overnight Saturated NaHCO$_3$ solution was added and the mixture was extracted with CH$_2$Cl2. The organic portion was dried (MgSO$_4$) and the solvent was removed under reduced pressure. The residue was purified by flash chromatography on silica gel (CH$_2$Cl$_2$/MeOH; 9:1) to give 4.39 g of an oil (61%). $^1$H-NMR (CDCl$_3$) ◻7.89–7.87(m, 1H,) 7.83 (d, 2H, J=8.0 Hz), 7.51 (t, 1H, J=7.8 Hz), 7.34 (s, 1H), 6.93–6.92 (m,2H), 3.82 (s, 3H), 2.80 (t, 2H, J=7.8 Hz) 2.59 (t, 2H, J=7.8 Hz), 2.33 (s, 6H). IR CHCl$_3$, 1357, 1115 $c^{m-1}$. The oxalate salt was prepared and recrystallized from an acetone/Et2O mixture; mp 224–226° C.

EXAMPLE 11

1-Benzenesulfonyl-5-methoxy-2-n-propyl-N,N-dimethyl tryptamine. A 2.5 M solution of nBuLi (1.4 mL, 3.5 mmol) was added in a dropwise manner to a stirred solution of 1-Benzenesulfonyl-5-methoxy-N,N,-dimethyltryptamine oxalate (free base) (1.00 g, 2.79 mmol) in DME (4 mL) at −10° C. under N$_2$. The resulting solution was allowed to stir for an additional 10 min at −10° C., and then nPrI (0.35 mL, 3.59 mmll) was added. The reaction mixture was allowed to stir for 1 h at −10° C. Saturated NaHCO$_3$ solution was added and the reaction mixture was extracted with CHCl2. The organic portion was washed with brine and dried (MgSO$_4$); the solvent was removed under reduced pressure and the residue was purified by flash chromatography on silica gel. (CH$_2$Cl$_2$/MeOH;30:1 ). To give 0.19 g of a bright yellow oil. $^1$H-NMR (CDCl$_3$) ◻ 8.06 (d, 1H, J=8.79 Hz), 7.62 (d, 2H, J=8.22 Hz), 7.51–7.46 (m, 1H), 6.89–6.85 (m, 1H), 3.85 (s, 3H), 2.96–2.89 (m, 4H) 2.63–2.57 (m, 2H), 2.48 (s, 6H) 6.87, 1.73 (q, 2H, J=7.51 Hz), 1.00 (t, 3H, J=7.51 Hz). IR CHCl$_3$, 1355 $c^{m-1}$.

EXAMPLE 12

5-HT Derivative Binding to 5-HT6 Receptor

The binding assay employed human 5-HT$_6$ stably transfected to HEK 293 human embryonic kidney cells with [$^3$H] lysergic acid diethylamide (70 Ci/mmol; Dupont NEN) as radioligand. Radioligand was diluted in incubation buffer in borosilicate glass vials and protected from light. Competing agents (1 mM stock solution) were dissolved in DMSO or saline and stored at −20° C. Dilutions of compounds were made using incubation buffer in 96-well plates and mixed by multichannel pipetting. Serial dilutions (1 in 4) started at a final concentration of 10,000 nM. Final concentrations>10, 000 nM were individually prepared from the 1 mM stock solution. Nonspecific binding was defined by 100 mM serotonin creatinine sulfate (Research Biochemicals) prepared fresh in incubation buffer at the time of each determination, and protected from light. in incubation buffer at the time of each determination, and protected from light. Reaction volumes were as follows: 200 ml incubation buffer (50 mM tris, 0.5 mM EDTA, 10 mM MgCl$_2$), pH 7.4 at 22° C., 100 ml test agent or serotonin (100 mM) or buffer, 100 ml [3H]lysergic acid diethylamide (2 nM final concentration) and 100 ml membrane preparation (15 mg protein). The incubation was initiated by the addition of membrane homogenate and the plates vortexed. The plates were incubated, with protection from light, by shaking at 37° C. for 60 min. The binding reaction was stopped by filtration. The samples were filtered under vacuum over 96 well glass fiber filters, presoaked in 0.3% PEI in 50 mM tris buffer (pH 7.4) for at least 1H and then washed 6× with 1 ml of cold 50 mM tris (40° C., pH 7.4) using a Packard Filtermate Harvester. The unifilter plates were dried overnight in a 37° C. dry incubator. The unifilter bottoms were sealed and 35 ml of Packard MicroScint was added. The plates were allowed to equilibrate for 1 h and were then sealed using a Packard TopSeal P with the Packard Plate Micromate 496. Plates were counted by liquid scintillation spectrometry. Each well was counted for 3 min. Compounds were initially assayed at 1000 and 100 nM. If a compound caused at least 80% inhibition of [$^3$H]lysergic acid diethylamide binding at 1000 nM, it was further tested and a Ki determined. The range of concentrations chosen was so that the middle concentration would produce approximately 50% inhibition.

Table 1 shows the affinity for 5-HT$_6$ receptors of claimed compounds derived from the general formula in formula 2 above.

| COMPOUND | R1 | R2 | R3 | R4 | R5 | Ki(nm) |
|---|---|---|---|---|---|---|
| A | Me | Me | 5-OMe | H | Me | 60 |
| B | Me | Me | 5-OMe | H | Et | 16 |
| C | Me | Me | 5-OMe | H | nPr | 185 |
| D | Me | Me | 5-OMe | H | Phenyl | 20 |

Table 2 shows the results of affinity for 5-HT$_6$ receptors of claimed compounds derived from the general formula in formula 3 above.

| COMPOUND | R1 and R2 | R4 | Ki(nm) |
|---|---|---|---|
| E | Me | —CH2-phenyl | 136 |
| F | H | —Ch2-phenyl | 302 |
| G | Me | H | 168 |
| H | Me | —SO2-phenyl | 2 |

Table 3 shows the results of affinity for 5-HT$_6$ receptors of claimed compounds derived from the general formula in formula 4 above.

| COMPOUND | X | Ki(nM) |
|---|---|---|
| I | O | 84 |
| J | H2 | 1030 |

EXAMPLE 13

Characterization of 5HT$_6$ Selectivity

Selected compounds were examined to determine their specificity of binding to the 5-HT$_6$ receptor. Compounds were examined at more than 30 receptor populations. Assays for the following receptors were performed as per the NIMH Psychoactive Drug Screening Program. The compounds failed to displace radioligand (i.e., <50% displacement) at a concentration of 10,000 nM at most receptors. Where more than 50% displacement was observed, Ki values were determined and the data are reported in the following table. It can be seen that the compounds are selective for 5-$HT_6$ receptors.

Table 4 shows the 5-selectivity of several compounds of the invention.

TABLE 4

| | Ki, nM(SEM) | | | |
|---|---|---|---|---|
| Receptor Population | COMPOUND A | COMPOUND B | COMPOUND D | CONTROL AND AGENT |
| NET | 6,380(3190) | >10,000 | >10,000 | Nortriptyline 6.3 (1.2) |
| SERT | >10,000 | >10,000 | 4,700(1550) | Fluoxetine 3.5(0.7) |
| h5-HT1A | 200(60) | 170(54) | 1,470(310) | WAY 1000,635 0.6 (1.5) |
| h5-HT1D | 250(180) | 290(700) | 6,225(70) | Ergotamine0.8 (0.6) |
| h5-HT1E | 1,800(600) | 520(180) | >10,000 | Serotonin0.5 (.015) |
| r5-HT2A | >10,000 | >10,000 | 470(10) | Clozapine 9(1) |
| r5-HT2C | 4,020(640) | 1,810(490) | 675(180) | Clozapine 23(5) |
| h5-HT5A | 10,450(2195) | 4,620(650) | 5,160(930) | Ergotamine 22(3) |
| b5-HT7 | 145(34) | 300(60) | 155(35) | Clozapine 9(2) |
| h5-Ht6 | 60(13) | 16(4) | 20(5) | Clozapine 10(3) |

Compounds displayed Ki values of >10,000 nM at the following populations of receptors: histamine, NMDA, PCP, acetylcholine, opiate, and vasopressin receptors. Ki values were >10,000 nM for compounds A and B at hD1,rD2,rD3, rD4, and hD5 receptors and 10,000 nM for D at hD1,rD2, and rD4 receptors. Compound D produced 70% inhibition at rD3 and hD5 receptors. NET and SERT represent the norepinephrine and serotonin transporters. Ki values for all three compounds were >10,000 at the dopamine transporter.

EXAMPLE 14 cAMP activation assays. Human 5-$HT_6$ receptors stably expressed in 293 HEK cells were grown in 24-well plates to near confluence and 18 h prior to the assay the medium was replaced with DMEM containing dialyzed 10% Fetal Calf Serum. For the assay, the medium was aspirated and replaced with fresh DMEM without serum and incubated with various concentrations of compounds of the invention in a total volume of 0.5 ml for 15 min. The assay was terminated by aspiration and the addition of 10% trichloroacetic acid (TCA). The TCA extract was used for cAMP determinations. (Data represent the mean of N=4 separate determinations). Results of cAMP activation by various compounds of the invention are shown in the attached Drawing of FIG. 1.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

Having thus described our invention, what we now claim as new and desire to secure by Letters Patent is as follows:

1. A method of treating a mental disorder in a patient mediated by the 5-$HT_6$ receptor, by administering an effective amount of a therapeutically effective composition comprising:

a pharmaceutically acceptable carrier; and a compound having the general structural formula

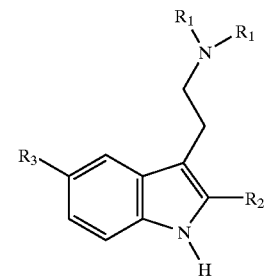

wherein $R_1$ is selected from the group consisting of hydrogen, methyl and lower alkyls other than methyl and may be the same or different at each site, $R_2$ is selected from the group consisting of ethyl, propyl and aryls, and $R_3$ is selected from the group consisting of hydrogen, methyl, methoxy, and lower alkyls.

2. A method for treating mental disorders in a patient for which a 5-$HT_6$ receptor antagonist is indicated comprising the step of administering to such a patient a pharmaceutical composition comprising a carrier, and a compound selected from the group consisting of 2-ethyl-5-methoxy-N,N-dimethyltryptamine maleate and 5-methoxy-2-phenyl-N,N-dimethyltryptamine oxalate.

* * * * *